(12) United States Patent
Roh et al.

(10) Patent No.: US 7,329,488 B2
(45) Date of Patent: *Feb. 12, 2008

(54) KIT FOR SEPARATING AND PURIFYING NUCLEIC ACIDS OR VARIOUS BIOLOGICAL MATERIALS, AND SYSTEM FOR AUTOMATICALLY PERFORMING SEPARATION OR PURIFICATION OF BIOLOGICAL MATERIALS USING THE SAME

(75) Inventors: Hee Joun Roh, Seoul (KR); Raehyuk Chang, Seoul (KR); Gi Young Jang, Seoul (KR)

(73) Assignee: Bionix, Inc. (KR)

( * ) Notice: Subject to any disclaimer, the term of this patent is extended or adjusted under 35 U.S.C. 154(b) by 514 days.

This patent is subject to a terminal disclaimer.

(21) Appl. No.: 10/440,791

(22) Filed: May 19, 2003

(65) Prior Publication Data

US 2004/0157224 A1 Aug. 12, 2004

(30) Foreign Application Priority Data

Jan. 29, 2003 (KR) .................. 10-2003-0005689

(51) Int. Cl.
*C12Q 1/68* (2006.01)
(52) U.S. Cl. .......................... 435/6; 435/91.1
(58) Field of Classification Search ............. None
See application file for complete search history.

(56) References Cited

U.S. PATENT DOCUMENTS

| 3,985,649 A | | 10/1976 | Eddelman |
| 4,683,195 A | | 7/1987 | Mullis et al. |
| 5,508,178 A | * | 4/1996 | Rose et al. ............... 435/91.1 |
| 6,140,110 A | * | 10/2000 | Vinayagamoorthy et al. .... 435/285.1 |
| 6,908,759 B2 | * | 6/2005 | Jang ...................... 435/285.1 |

* cited by examiner

*Primary Examiner*—Gary Benzion
*Assistant Examiner*—Heather Calamita
(74) *Attorney, Agent, or Firm*—Blakely Sokoloff Taylor & Zafman

(57) ABSTRACT

The present invention relates to a kit for separating and purifying nucleic acids or a variety of biological materials and a system for automatically performing the operations of separating and purifying a variety of biological materials using the kit. The kit of the present invention comprises a container with a plurality of chambers formed in a row for containing buffers and solid materials suitable for separating the nucleic acids or biological materials from the biological samples, and a carriage including a flat portion with a hole formed therethrough and a projection having an inside passage of which one end is closed and the other end is open and having a predetermined length such that the projection can be dipped into the buffers. A mounting means is formed on the flat portion of the carriage such that the carriage can be detachably mounted to a transport means for transferring the carriage to the respective chambers. Further, a system for automatically performing the separation and purification using the kit is also provided. According to the present invention, a predetermined number and a small amount of samples can be selectively processed in accordance with a user's needs. Therefore, the samples are quickly processed and prevented from being unnecessarily wasted, and thus, processing efficiency can be improved.

13 Claims, 5 Drawing Sheets

(a)

(b)

KIT FOR SEPARATING AND PURIFYING NUCLEIC ACIDS OR VARIOUS BIOLOGICAL MATERIALS, AND SYSTEM FOR AUTOMATICALLY PERFORMING SEPARATION OR PURIFICATION OF BIOLOGICAL MATERIALS USING THE SAME

BACKGROUND OF THE INVENTION

1. Field of the Invention

The present invention relates to a kit for separating and purifying nucleic acids or a variety of biological materials and a system for automatically performing the operations of separating and purifying a variety of biological materials using the kit.

2. Description of the Prior Art

Machines for separating and purifying nucleic acids or biological materials from blood or other biological samples have been widely used in a variety of fields such as biology, biochemistry, molecular medicine, forensic medicine, medical diagnostics, etc.

Recently, Polymerase Chain Reaction (herinafter, referred to as "PCR") for DNA amplification, which became the foundation for the rapid development of genetic engineering, has been frequently used as an essential step in both biological research and diagnostic fields (Sec U.S. Pat. No. 4,683,195). Conventional methods for isolating nucleic acids generally involve organic solvents such as phenol and chloroform. Further, several methods have been proposed using materials that have the property of binding nucleic acids. Concrete examples of these materials are silica, glass fibers, anion exchange resins and modified magnetic beads.

The methods using these materials have advantages in that no harmful organic solvents are involved, that physical and biochemical degradation of nucleic acids during the isolation process is minimized, and that immobilized nucleic acids are less susceptible to digestion by nucleic acid-degrading enzymes. The aforementioned methods, however, still need intensive manual pipetting steps to transfer the solid materials to other vessels or containers. Thus, there is a problem in that the operator is vulnerable to potential viral and bacterial infection if infected blood or bacteria is the starting material of nucleic acid isolation.

In order to solve these problems, eliminate experimental errors due to manual operation and obtain more reliable measurement results, several automatic machines such as "MagNa Pure LC" (Roche, Switzerland) were developed to perform a large number of sample manipulations based on the concept disclosed in U.S. Pat. No. 3.985.649. Most of these automatic machines utilize magnetic beads lo eliminate the use of harmful chemical solvents and centrifugation steps when collecting nucleic acids or biological materials from various biological samples. Although these large automatic machines are adequate for high throughput isolation of the nucleic acids or biological materials, they care also bulky, expensive, rather complicated, and inefficient for a small or medium number of sample manipulations. As a result, these machines are not practical for most diagnostic clinical and small research laboratories.

Further, small and medium automatic machines such as "KingFisher" (Thermo Labsystems, Massachusetts, USA) and SX-6G (PSS, Chiba, Japan), designed for processing a relatively small amount of samples have been recently developed. These automatic machines have been designed in such a manner that a total amount of samples can be processed when performing sample measurement or processing operations, however, there is still another problem ill that they are not yet efficient for measurement of only a predetermined number of samples. That is, there is still a need for a small and portable automatic machine capable of selectively processing the necessary number of samples if necessary.

SUMMARY OF THE INVENTION

The present invention is contemplated to solve the problems related with conventional machines for separating nucleic acids or biological materials from a variety of biological samples according to the prior arts.

An object of the present invention is to provide a novel kit wherein appropriate materials, such as solid materials, buffers and enzymes, needed for separating or purifying nucleic acids or biological materials from biological samples are beforehand filled in a plurality of chambers of the kit which scan be selectively used as necessary.

Another object of the present invention is to provide an automated sample processing system capable of selectively processing the necessary number of samples using the kit.

According to an aspect of the present invention for achieving the above objects, there is provided a kit for use in a system for automatically processing nucleic acids or biological materials from biological samples using solid materials. The kit of the present invention comprises a container with a plurality of chambers formed in a row for containing buffers and the solid materials suitable for separating the nucleic acids or biological materials from the biological samples, and a carriage including a flat portion with a hole formed therethrough and a projection having an inside passage of which one end is closed and the other end is open and having a predetermined length such that the projection can be dipped into the buffers, wherein a mounting means is formed on the flat portion of the carriage such that the carriage can be detachably mounted to a transport means for transferring the carriage to the respective chambers.

According to another aspect of the present invention, there is provided a system for processing nucleic acids or biological materials from biological sample using a desired number of lie kits. The system of the present invention comprises a base plate on which the desired number of containers with a series of chambers can be selectively installed in accordance with a test object; a carriage attachment frame assembly including a frame through which a plurality of holes are formed in accordance with a predetermined arrangement of the containers installed on the base plate, and a plurality of mounting means which are formed on a bottom surface of the frame correspondingly to the mounting means of the carriages such that the carriages of the kits can be selectively attached to or detached from the frame in accordance with the predetermined arrangement; a magnetic bar assembly including a frame with a plurality of magnetic bars attached to a bottom surface of the frame to correspond to the holes formed through the frane of the carriage attachment frame assembly; a base plate transport unit for horizontally moving the base plate on which the containers have been selectively arranged; a carriage attachment frame assembly transport unit for vertically moving the carriage attachment frame assembly to mix or stir buffers and solid materials in the chambers; a magnetic bar transport unit for vertically moving the magnetic bars of the magnetic bar assembly through the holes and inside passages of the carriages; and a control unit for controlling the transport units in accordance with a predetermined separation and processing procedure.

BRIEF DESCRIPTION OF THE DRAWINGS

The above and other objects and features of the present invention will become apparent from the following description of preferred embodiments given in connection with the accompanying drawings, in which.

DETAILED DESCRIPTION OF THE INVENTION

Thereinafter, preferred embodiments of the present invention will be explained in detail with reference to the accompanying drawings.

Figure 1:
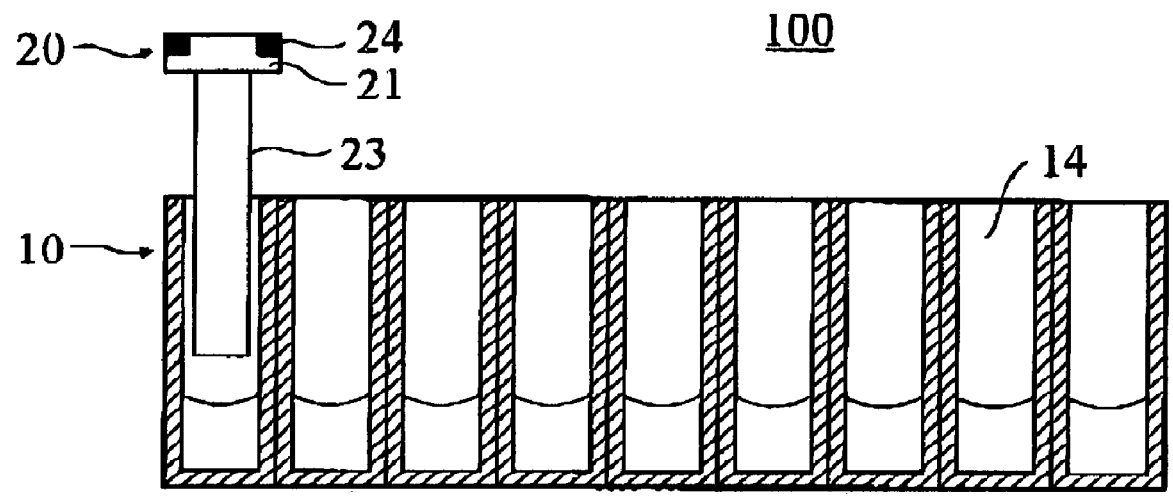
FIG. 1 is a sectional view of a kit according to the present invention.
Figure 2:
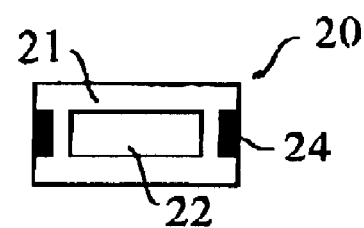
FIG. 2 is a plan view illustrating, a detailed configuration of a carriage in the kit shown in FIG. 1.

FIGS. 1 and 2 specifically show a kit for use in separating nucleic acids and biological materials from biologic samples according to the present invention.

As shown in FIG. 1, the kit 100 of the present invention comprises a rectilinear container 10 including a plurality of chambers 14, and a carriage 20 with a projection 23 configured to be inserted into each of the chambers 14 of the container 10. Solid materials and buffers suitable for the separation of nucleic acids or biological materials are contained in the respective chambers 14 of the container 10, which ar arranged in a row in tie container 10. Further, the carriage 20 includes a flat portion 21 with a hole 22 formed therethrough, and a projection 23 including an inside passage of which one end is closed and the other end is open and having a predetermined length so that the blind end can be dipped into the buffers in the chamber 14. Furthermore, as best shown in FIG. 2, a mounting means 24 is installed on the flat portion 21 of the carriage 20 such that the carriage 20 can be detachably mounted to a carriage attachment frame assembly 30 (Refer to FIGS. 3 and 4 to be described later). Such a mounting means 24 may be configured in the form of a general magnet, rubber magnet, neodymium magnet, or magnetic metal body. Since the mounting means of the carriage can be attached to a complimentary magnet-type mounting means of the carriage attachment frame assembly 30, the carriage 20 can also be attached to the carriage attachment frame assembly 30. Consequently, the carriage 20 can be transferred in accordance with a predetermined sample processing procedure.

The chambers 14 of the container 10 have a generally rectangular sectional shape for space efficiency, but need not be limited thereto. For example, the sectional shape may be circular or oval. In addition, the sectional shape of the projection 23 of the carriage 20 need not be necessarily limited thereto, but preferably corresponds to that (if the chamber 14.

A plurality of containers 10 of the kit 100 can be selectively mounted to a base plate 50 by the predetermined number necessary for the given separation and purification test. Accordingly, the predetermined number of containers 10 can be moved on a horizontal plane in accordance with the predetermined procedures by a base plate transport means 80 (refer to FIG. 4) to be described later.

As specifically shown in FIG. 2, the mounting means 24 such as magnets are formed on both sides of a top surface of the flat portion 21 so that the carriage 20 can be easily attached to the carriage attachment frame assembly 30. But, the present invention is not necessarily limited thereto, and may be configured in such a manner that the mounting means is formed in the interior of the flat portion 21 of the carriage 20. Of course, so far as it may be detachably and stably attached to the carriage attachment frame assembly 30, any kind of well-known mounting means such as Velcro fasteners can be employed in the present invention.

Further, solid materials, buffers, and the like may be filled beforehand into the respective chambers 14 of the container 10 in accordance with a predetermined procedure so that inexperienced users who are not skillful in the processing of nucleic acids and biological materials from biological samples can easily perform the procedure. It is preferred that the solid materials be magnetic beads for allowing the nucleic acids or biological materials to be easily collected or transferred.

Moreover, it is also preferred that the container 10 and the carriage 20 be made of materials such as polycarbonate, polypropylene, polystyrene, and acrylonitrile-butadione-styrene (ABS) for easy manufacture of the kit and minimization of chemical reaction with the solid materials and buffers.

A system for automatically separating and purifying tho nucleic acids and biological materials using the aforementioned kit will be now explained with reference to FIGS. 3 and 4.

A means, which is used for processing the solid materials in accordance with the predetermined procedure and transferring the processed materials so as to collect and transfer the nucleic acids and biological materials in the container 10 of the kit 100, is first explained.

Figure 3:
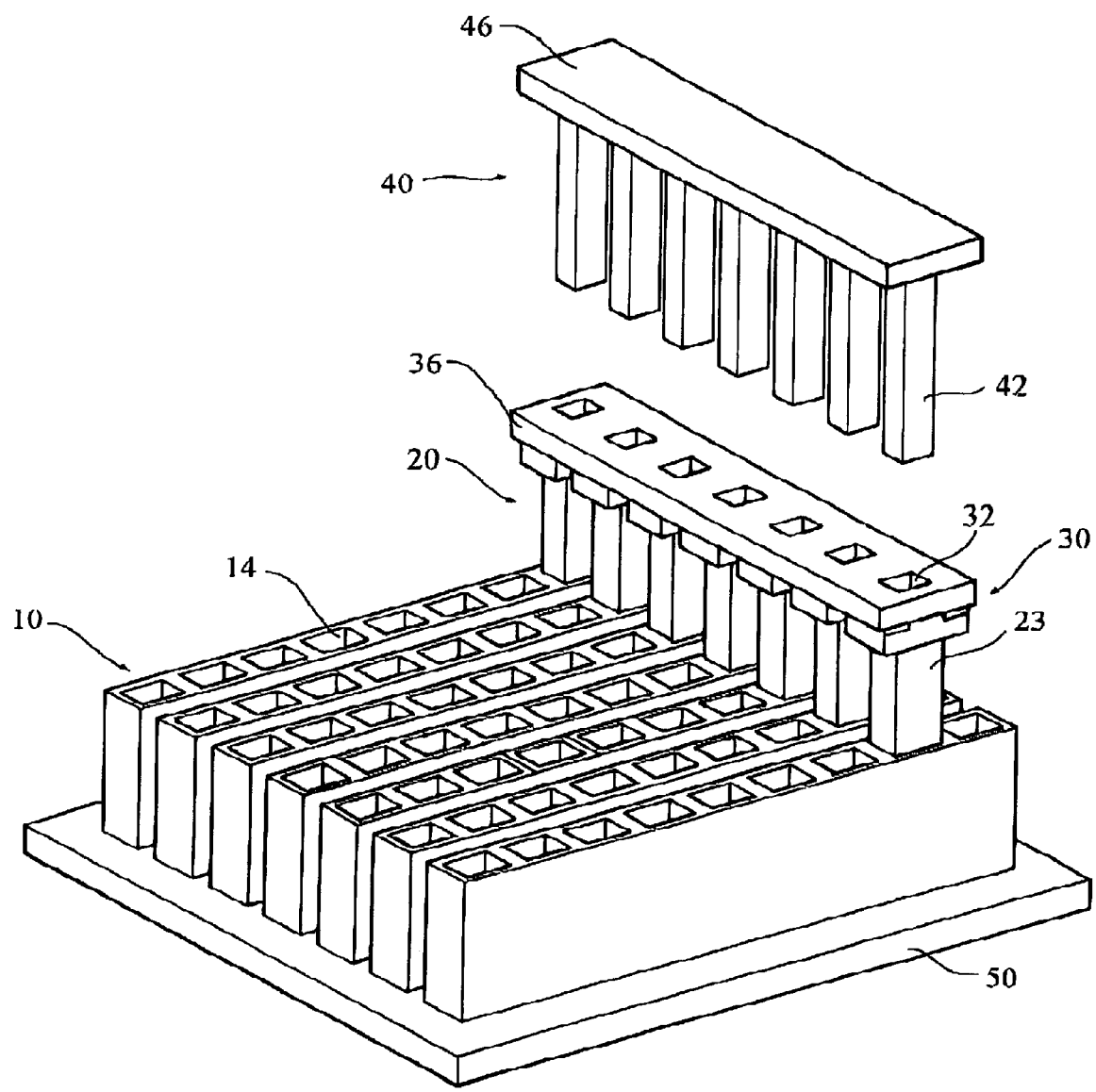
FIG. 3 is a perspective view illustrating the kit shown in FIG. 1 and several components of an automation system used with the kit.
Figure 4:
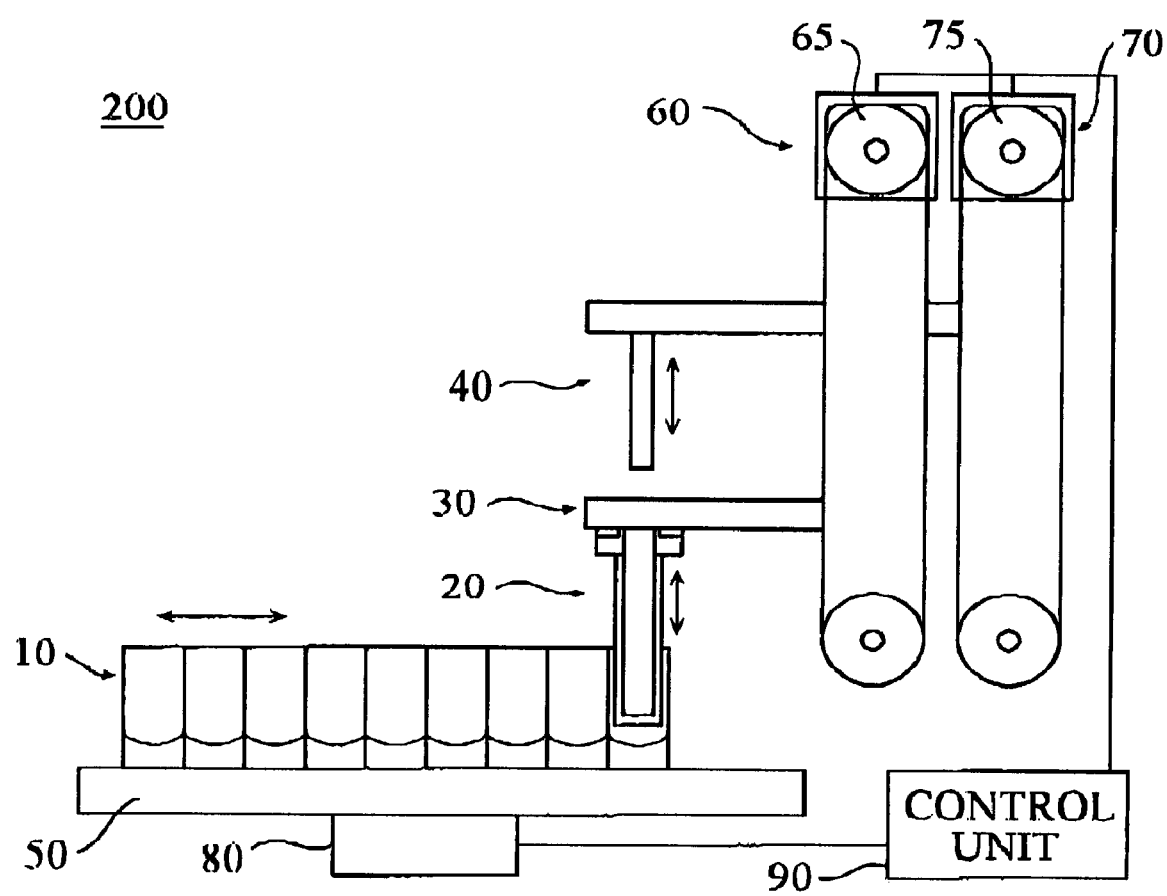
FIG. 4 slows the entire configuration of the automation system in which a given number of kits according to the present invention are installed.

FIG. 3 is a perspective view showing a state where the carriage attachment frame assembly 30 and a magnetic bar assembly 40 are used with the kit 100. The carriage attachment frame assembly 30 is used to selectively mount the aforementioned carriage 20, and the magnetic bar assembly 40 includes magnetic bars 42 for allowing biological materials such as nucleic acids to be processed using solid materials such as the magnetic beads in a state where the carriage 20 is attached to the magnetic bar assembly 40.

As shown in FIG. 3, the carriage attachment frame assembly 30 Includes a flat portion 36 (hereinafter, referred to as the "lower frame"). The lower frame 36 is configured in such a manner that each hole 32 is connected with the hole 22 of the carriage 20 and magnet-type mounting means are also formed at positions corresponding to those of the magnets 24 of the carriage 20. As explained in connection with the carriage 20, the complementary mounting means of the lower frame may be formed on a bottom surface of the lower frame 36 and also be formed in the interior of the lower frame 36, if necessary. Of course, any other kind of detachable mounting means such as described above in connection with the carriage may be provided instead of using magnets.

In addition, the magnetic bar assembly 40 placed or arranged above the carriage attachment frame assembly 30 includes a flat portion 46 (hereinafter, referred to as the "upper frame"). The magnetic bars 42 extending vertically downward by a predetermined length are formed at positions corresponding to those of the holes 32 of the carriage attachment frame assembly 30 on a bottom surface of the upper frame 46. Each of the magnetic bars 42 is configured to enter the inside passage of the projection 23 of the carriage 20 through the relevant holes 32 and 22 of the carriage attachment frame assembly 30 and the carriage 20. As will be described later, it is preferred that the length of each magnetic bar 42 be formed somewhat longer than the distance from the bottom surface of flat portion 21 of the carriage 20 to the lowermost end of each projection 23 so that the user can cause the carriage 20 to be easily detached from the carriage attachment frame assembly 30 if necessary.

The automation system will be now explained in detail with reference to FIG. 4. The system 200 comprises a base plate 50 on which the predetermined number of containers 10 of the kit 100 can be installed in accordance with a test object, the carriage attachment frame assembly 30 for mounting the predetermined number of carriages 20 of the kit 100 thereto, the magnetic bar assembly 40, a carriage attachment frame transport unit 60 for moving the carriages 20 and the carriage attachment frame assembly 30 in a vertical direction, a magnetic bar assembly transport unit 70 for moving the magnetic bar assembly 40 in the vertical direction, a base plate transport unit 80 for moving the base plate 50 in a horizontal direction, and a control device 90 for controlling all the transport units.

In general, the carriage attachment frame transport unit 60 causes the carnage attachment frame assembly 30 to be belt-driven through a first motor 65, and the magnetic bar assembly transport unit 70 causes the magnetic bar assembly 40 to be belt-driven through a second motor 75. Further, the base plate transport unit 80 causes the base plate 50 to be gear-driven through a third motor (not shown). Of course, any other kind of means such as belts or gears may be employed as a means of transport.

As described above, each of the carriages 20 can be transferred by the carriage attachment frame transport unit 60 in a state where the mounting means 24 installed on the flat portion 21 are attached to the complementary mounting means installed on the lower frame 36, and the projection 23 can be dipped into the relevant chamber of the container 10 when the flat portion 21 of the carriage 20 approaches the top surface of the container 10. When the carriage 20 moves upward and downward, therefore, the buffers (e.g., liquid reagents) and the solid materials can be mixed or stirred effectively in each relevant chamber 14 by means of each projection 23. Other means for allowing the container 10 to be shaken may be provided to more effectively agitate or mix the solid materials and the buffers.

Further, in order to collect the solid materials in the relevant chamber 14 and then transfer the collected solid materials to the next chamber, each of the magnetic bars 42 of the magnetic bar assembly 40 is inserted through the hole 22 and the inside passage of the projection 23 or the relevant carriage 20 to come into contact with a lowermost end wall of the projection 23 by means of downward transport movement of the magnetic bar assembly transport unit 70. At this time, it is preferred that the magnetic bar assembly transport unit 70 be in synchronization with the carriage attachment frame transport unit 60. and thus, the magnetic bars 42 of the magnetic bar assembly 40 are moved into the chambers 14 of the container 10 together with the carriages 20. That is, when the flat portions 21 of the carriages 20 come into contact with the top surface of the container 10 in a state where distal ends of the magnetic bars 42 of the magnetic bar assembly 40 are in contact with the inner lowermost end walls of the projections 23 of the carriages 20, the projections 23 of carriage 20 are dipped into the buffers in the chambers 14. Therefore, the solid materials in the relevant chamber 14 are attracted and attached to an outer surface of the projection 23 by means of magnetic force from the magnetic bar 42 so that the solid materials such as the magnetic beads can be properly collected. Then, the carriages 20 etc. are raised to a certain extent that the container 10 can be moved without interference from the projections 23 of the carriages 20, and the base plate 50 with the container 10 installed thereon is horizontally moved by a horizontal distance corresponding to a predetermined pitch thereof using the base plate transport unit 80. Subsequently, the carriage attachment frame assembly 30 and the magnetic bar assembly 40 are lowered into the next chamber to perform the next process. By repeating the aforementioned process. predetermined procedures can be automatically performed by the control unit 90. Therefore, final components such as the nucleic acids or biological materials can be easily obtained in the final chambers.

A microcomputer may be generally used as the control unit 90 for controlling the predetermined procedure and the transport units. Of course, a microchip for performing the same object as the control unit may also be employed. Since the configuration and operation of the control unit 90 are substantially identical to those of the conventional control unit, a detailed description thereof will be omitted.

Furthermore, after completion of a portion of the procedure such as the separation and purification of the nucleic acids or biological materials or at a proper time the user wants, the carriage 20 should be able to be detached from the carriage attachment frame assembly 30. As described above, in order to cause the carriage 20 to be easily detached from the carriage attachment frame assembly 30, the longitudinal length of each of the magnetic bars 42 should be a little greater than the distance from the bottom surface of thc flat portion 21 of the carriage 20 to the lowermost end of the projection 23. That is, by configuring a control program or performing a manual operation such that the relevant magnetic bar 42 of the magnetic bar assembly 40 can be fully inserted into the inside passage of the projection 23 through tho hole 32 of the carriage attachment frame assembly 30 and the hole 22 of the carriage 20 at a desired time of period, the magnetic bar 42 is configured Lo push against the inner lowermost end wall of the projection 23 of the carriage 20. Thus, since the pushing action can overcome the magnetic force of the magnet-type mounting means, the carriage 20 can be separated from the carriage attainment frame assembly 30. Accordingly, the kit 100 containing the final components obtained according to the predetermined procedures can be used in an additional necessary process.

Figure 5:
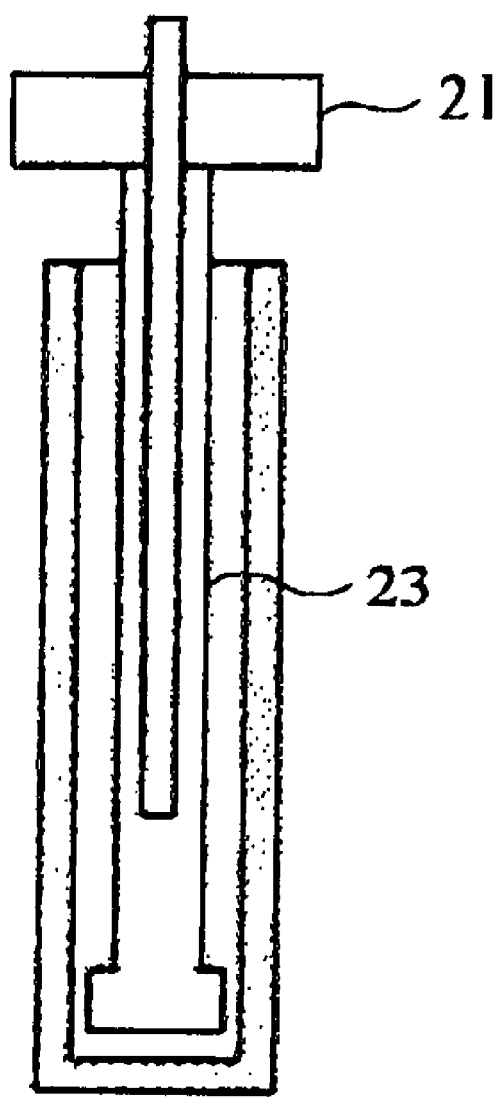
FIG. 5 is a view of a carriage in a kit according to a modified embodiment of the present invention.
Figure 5:
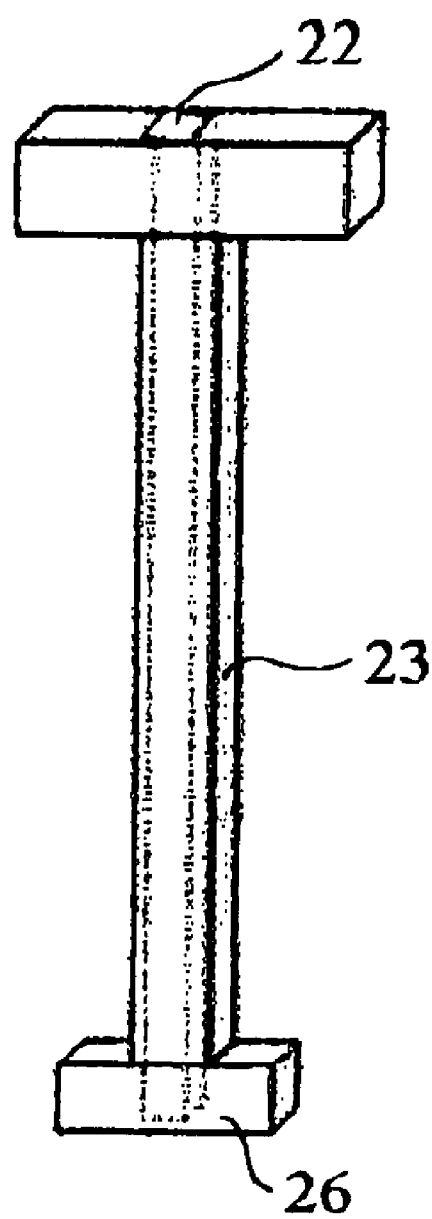
Figure 6:
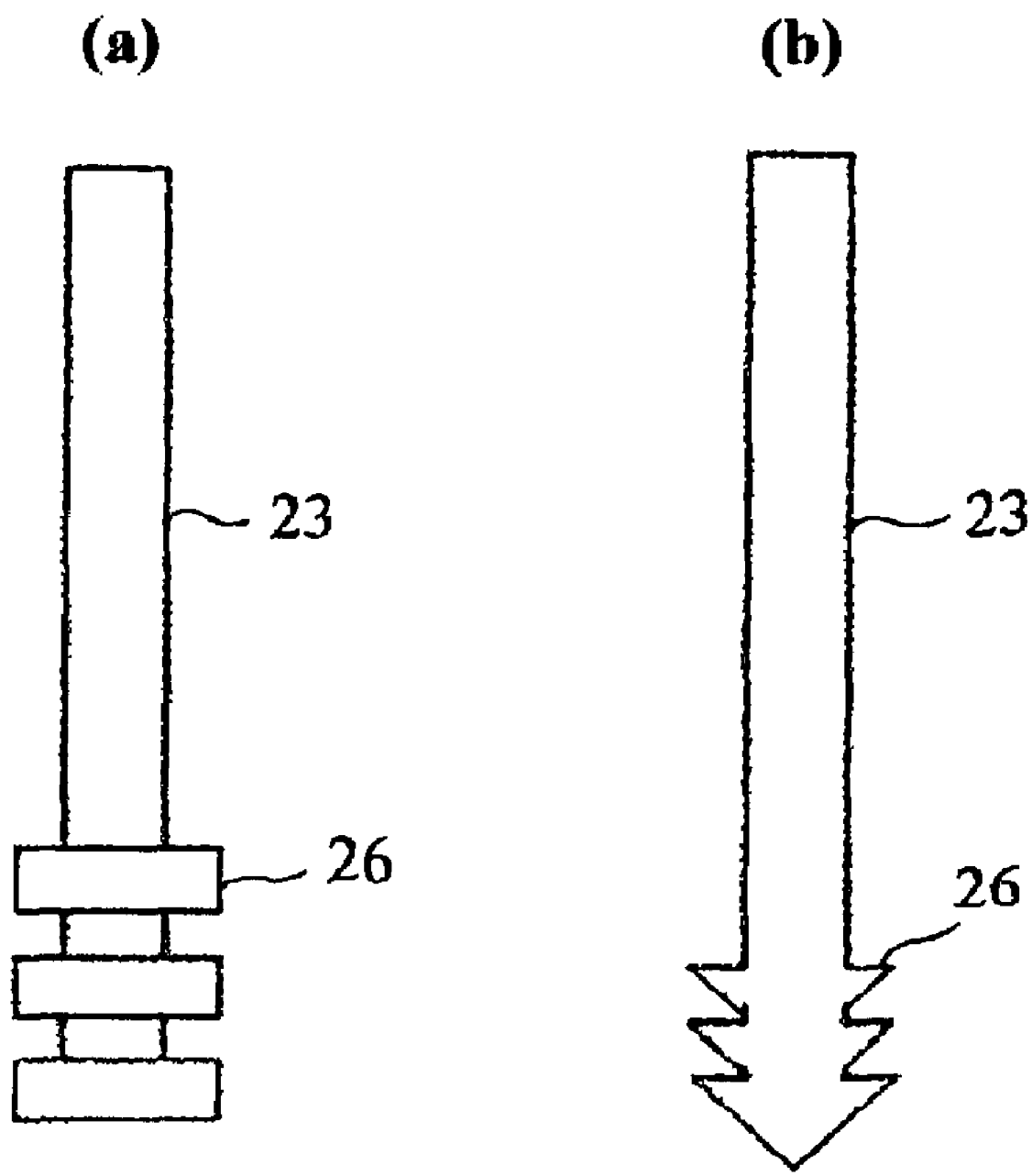
FIG. 6 is a view of a carriage in a kit according to another modified embodiment of the present invention.

In the meantime, the configuration and shape of the carriage exert a great influence on the amount of samples and magnetic particles adhering to the surface of the carriage as well as how well the samples can be mixed in the chambers of the container. FIGS. 5 and 6 show other preferred embodiments of the carriage of the kit according to the present invention, which has been modified for improving the mixing or stirring performance.

As shown in FIGS. 5 and 6, the carriage 20 of the kit 100 according to the present invention is configured to include a bulged portion 26, which has a sectional area greater than a horizontal sectional area of the projection 23, at the lower end of the projection 23. Thus, since the bulged portion 26 of the carriage 20 having the horizontal sectional area greater than that of the projection 23 enters the chamber 14 of the container 10, a liquid stream flowing around the bulged portion 26 becomes stronger, and thus, the liquid can be well mixed or stirred. In addition, since a predetermined vortex-forming space is provided behind the bulged portion 26 of the carriage 20, the mixing process is further accelerated. In order to further improve this mixing effect, two or more bulged portions 26 may be arranged in a row in a longitudinal direction of the carriage 20. Moreover, it is preferred that a bottom surface of the bulged portion 26 has a shape exactly corresponding to that of the chamber 14 of the container 10 (e.g., flat, hemispherical, conical, and the like) such that the liquid can be vigorously mixed and a great deal of the magnetic particles can adhere to the bulged portion 26.

Although it has not yet shown and illustrated in the figures, grooves or protrusions may be formed on the floor surface of the bulged portion 26 of the carriage 20 of the present invention so that the carriage 20 cannot be inadvertently detached from the carriage attachment frame assembly 30 due to the adhesion force of the bottom surface of the bulged portion 26 with the liquid residing within the chamber when the carriage 20 fully enters and retracts from the chamber 14 of the container 10.

In particular, the carriage 20 with the bulged portion 26 constructed as such can be used with liquid samples and also with solid samples such as plants, insects or animal tissues. That is, since the bulged portion 26 is formed to be larger than the carriage projection 23 in a radial direction of the carriage and to have its bottom surface corresponding to that of the chamber 14, the bulged portion 26 can cause leaves of the plants and the insects to be crushed and pulverized directly in the relevant chamber so that they become biological samples suitable for the isolation of nucleic acids or other biological materials. Thus, samples such as plants, insects or animal tissues may be applied directly to the kit of the present invention.

According to the present inventions a predetermined number of the kits, which include the carriage and the container with a plurality of chambers filled beforehand with buffers, solid materials, enzymes and the like in accordance with the object or test or experiment, can be selectively installed on the base plate. Thus, the manual operation of the user who is not skillful in performing clinical or biological tests or experiments is not required, and a small or medium number of samples can be very efficiently manipulated.

As a result, the small amount of samples can be quickly processed, and thus, there is an additional advantage in that unnecessary waste of samples can be avoided.

Further, the bulged portion is formed at the lower end of the carriage in such a manner that it has a horizontal sectional area greater than that of the projection plants or insects and its bottom surface corresponds to that of relevant chamber of the container. Thus, there are advantages in that liquid in the chamber is well mixed when the carriage enters the chamber and that solid samples such as the plants, insects or animal tissues can be used directly in the kit of the present invention.

While the invention has been shown and described with respect to the preferred embodiments, it will be understood by the skilled in the art that various changes and modifications may be made thereto without departing from the spirit and scope of the invention defined by the appended claims. Accordingly, the present invention should be construed as including the inventions defined by the appended claims and the equivalents thereof.

What is claimed is:

1. A kit for use in a system for automatically processing nucleic acids or biological materials from biological samples using solid materials, comprising:
   a container with a plurality of chambers formed in a row for containing buffers and the solid materials suitable for separating the nucleic acids or biological materials from the biological samples; and
   a carriage including a flat portion with a hole formed therethrough and a projection having an inside passage of which one end is closed and the other end is open and having a predetermined length such that the projection can be dipped into the buffers in the chambers,
   wherein a mounting means is formed on the flat portion of the carriage such that the carriage can be detachably mounted to a transport means for transferring the carriage to the respective chambers.

2. The kit as claimed in claim 1, wherein the container and carriage are made of a material selected from a group consisting of polycarbonate, polypropylene polystyrene and acrylonitrile-butadiene-styrene (ABS).

3. The kit as claimed in claim 1, wherein the solid materials are magnetic beads used for collecting or transferring the nucleic acids or biological materials.

4. The kit as claimed in claim 3, wherein the hole and inside passage of the carriage are a path through which magnetic bars for picking up the magnetic beads are vertically moved.

5. The kit as claimed in claim 1, wherein the mounting means is a magnet.

6. The kit as claimed in claim 1, wherein a bulged portion having a horizontal sectional area greater than that of the projection is further formed at a lowermost of the projection of the carriage wherein the bulged portion is integral with the projection.

7. The kit as claimed in claim 6, wherein at least two bulged portions are formed in a longitudinal direction of the carriage.

8. The kit as claimed in claim 6, wherein a bottom surface of the bulged portion of the carriage is shaped to substantially correspond to a shape of a floor surface of the chamber such that vigorous flow in the chamber and a strong crushing and pulverizing function for biological samples between the bottom surface of the bulged portion and the floor surface of the chamber can be ensured when the carriage fully enters the chamber.

9. The kit as claimed in claim 6, wherein protrusions or grooves are formed on a bottom surface of the bulged portion or a floor surface of the chamber.

10. The kit as claimed in claim 8, wherein the biological samples include solid samples.

11. The kit as claimed in claim 10, wherein the solid samples include plants.

12. The kit as claimed in claim 10, wherein the solid samples include insects.

13. The kit as claimed in claim 10, wherein the solid samples include animal tissues.

* * * * *